United States Patent [19]

Mosher, Jr. et al.

[11] Patent Number: 5,480,877

[45] Date of Patent: Jan. 2, 1996

[54] USE OF LYSOPHOSPHATIDIC ACIDS TO ENHANCE FIBRONECTIN BINDING

[75] Inventors: Deane F. Mosher, Jr.; William J. Checovich, both of Madison, Wis.

[73] Assignee: Wisconsin Alumni Research Foundation, Madison, Wis.

[21] Appl. No.: 422,738

[22] Filed: Apr. 14, 1995

Related U.S. Application Data

[63] Continuation of Ser. No. 146,246, Nov. 2, 1993, abandoned.

[51] Int. Cl.[6] ..................................................... A61K 31/66
[52] U.S. Cl. ................................ 514/134; 514/2; 514/8; 514/21
[58] Field of Search ........................... 514/134, 2, 8, 514/21, 558, 560

[56] References Cited

U.S. PATENT DOCUMENTS 5,238,839  8/1993  Cantor .................................. 435/240.1

OTHER PUBLICATIONS

W. Checovich, et al., Lipoproteins Enhance Fibronectin Binding to Adherent Cells, 12 Arterios. & Thromb. 1122–1130 (1992).

B. L. Allen–Hoffmann, et al., Transforming Growth Factor β Increases Cell Surface Binding and Assembly of Exogenous (Plasma) Fibronectin by Normal Human Fibroblasts, 8 Mol. Cell. Biol. 4234–4242 (1988).

R. Hynes, et al., Integrins: Versatility, Modulation, and Signaling in Cell Adhesion, 69 Cell 11–25 (1992).

J. Labat–Robert, et al., Comparative Distribution Patterns of Type I and III Collagens and Fibronectin in Human Arteriosclerotic Aorta, 33 Path. Biol. 261–265 (1985).

D. Mosher, et al., In Vitro Formation of Disulfide–bonded Fibronectin Multimers, 258 J. Biol. Chem. 6595–6601 (1983).

P. McKeown–Longo, et al., Interaction of the 70,000–mol–wt Amino–terminal Fragment of Fibronectin with the Matrix–assembly Receptor of Fibroblasts, 100 J. Cell Biol. 364–374 (1985).

A. Allio, et al., Extracellular Matrix Assembly of Cell–Derived and Plasma–Derived Fibronectins by Substrate–Attached Fibroblasts, 135 J. Cell. Physiol. 459–466 (1988).

A. Ridley, et al., The Small GTP–Binding Protein rho Regulates the Assembly of Focal Adhesions and Actin Stress Fibers in Response to Growth Factors, 70 Cell 389–399 (1992).

S. Smyth, et al., Fibrinogen Binding to Purified Platelet Glycoprotein IIb–IIIa (Integrin $\alpha_{IIb}\beta_3$) Is Modulated by Lipids, 267 J. Biol. Chem. 15568–15577 (1992).

O. Lowry, et al., Protein Measurement with the Folin Phenol Reagent, 193 J. Biol. Chem. 265–275 (1951).

D. Mosher, Assembly of fibronectin into extracellular matrix, 3 Curr. Opin. Struct. Biol. 214–222 (1993).

*Primary Examiner*—Gollamudi S. Kishore
*Attorney, Agent, or Firm*—Quarles & Brady

[57] ABSTRACT

Lysophosphatidic acids are used to enhance fibronectin binding. This assists in the process of wound healing. The acids are exogenously supplied. In one aspect, a kit is provided containing a skin salve that contains the acid or a salt thereof.

1 Claim, 2 Drawing Sheets

USE OF LYSOPHOSPHATIDIC ACIDS TO ENHANCE FIBRONECTIN BINDING

This invention was made with United States Government support awarded by the National Institutes of Health (NIH), Grant no. HL21644. The United States Government has certain rights in this invention. This application is a continuation of application Ser. No. 08/146,246, filed Nov. 2, 1993, abandoned.

FIELD OF THE INVENTION

The present invention relates generally to the use of certain phospholipids to enhance fibronectin binding to adherent cells. More specifically, the invention relates to the use of lysophosphatidic acids for that purpose.

BACKGROUND OF THE INVENTION

In humans and other mammals, fibronectin is a dimeric glycoprotein found at high concentrations in plasma and other body fluids. D. Mosher et al., Fibronectin, New York, Academic Press Inc. (1989); R; Hynes, Integrins: Versatility, modulation, and signaling in cell adhesion, Cell 69:11–26 (1982). The disclosure of these publications and of all other publications referred to herein are incorporated by reference as if fully set forth herein.

Soluble protomeric fibronectin is found at high concentrations in plasma and other body fluids and is synthesized and secreted in vitro by many cell types. Insoluble fibronectin consists of high molecular weight disulfide-stabilized multimers of fibronectin and is found in connective tissue, basement membranes and extracellular matrices. It mediates many important biological functions. Some of these are cellular migration during embryogenesis, wound healing and tumor metastasis. J. Labat-Robert et al., Comparative distribution patterns of Type I and III collagen and fibronectin in human arteriosclerotic aorta, Pathol. Biol. (Paris) 33, 261–265. (1985); R. Colvin, Fibronectin in wound healing. In Fibronectin. D. F. Mosher, ed. (New York: Academic Press) pp. 213–254 (1989); R. Hynes, Integrins: Versatility, modulation and signaling in cell adhesion, Cell 69, 11–26 (1992).

Insolubilization of cellular fibronectin is initiated by the reversible binding of soluble fibronectin to cell surfaces. Bound fibronectin is subsequently deposited into high-molecular-weight fibronectin multimers. Thus, the process of fibronectin matrix assembly is a stepwise process.

In the first step, soluble protomeric fibronectin reversibly binds to a putative cell surface matrix assembly receptor via an amino-terminal 70 KDa region of fibronectin. Once fibronectin has bound to the cell surface, additional fibronectin domains may participate in matrix assembly. In particular, fibronectin-fibronectin interactions may serve to further stabilize fibronectin binding and assure proper alignment of the incoming fibronectin. Finally, the fibronectin is stabilized within the fibril. Fibronectin matrix assembly (and thus wound healing, tumor metastasis, etc.) depends upon the fibronectin first efficiently and effectively binding to cell surfaces.

Certain serum components have been reported to improve fibronectin binding to a fibroblastic monolayer culture. This correlates with the finding that transformed hamster cells grown in 5% serum exhibit increased fibronectin deposition compared to cells grown in 0.3% serum. A serum component, transforming growth factor $\beta$, has been found to increase cell surface binding and assembly of exogenous plasma fibronectin by fibroblasts. See B. Allen-Hoffmann, et al., Transforming Growth Factor $\beta$ Increases Cell surface Binding and Assembly of Exogenous (Plasma) Fibronectin by Normal Human Fibroblasts, MCB 8, 4234–4242 (1988). Recently, our lab identified lipoproteins as additional enhancers of fibronectin binding to adherent cells. W. Checovich, et al., Lipoproteins Enhance Fibronectin Binding to Adherent Cells. Arterioscl. and Thromb. 12:1122–1130 (1992).

However, multi-component materials (e.g. serum; lipoproteins) cannot be used efficiently for certain applications (given that they have many components in them unrelated to fibronectin binding), and certain serum components have undesirable properties.

In unrelated research, there have been various studies of lysophosphatidic acids ("LPA"). As shown in FIG. 1 (1oleoyl, lysophosphatidic acid), a lysophosphatidic acid is an acid in which only one of the hydroxyl groups of the glycerol is esterified. Historically, the prefix lysoderives from the fact that the acids are often good detergents (and as such often can "lyse" cells). However, more generically, they are phosphatidic acids where the carbon is not esterified and the "3" carbon is bound to the $O—PO_3H_2$ group, or in the case of the salt one or more hydrogens are replaced (e.g. with $Na^+$). The "1" carbon will contain an acyl ester (in nature typically $C_{10}$–$C_{30}$; most often $C_{14}$–$C_{24}$) of fatty acids. Preferred LPAs are 1-acyl-SN-glycerol-3 phosphates.

Extracellular LPA is known to evoke diverse physiological responses, such as platelet aggregation, smooth muscle contraction, and fibroblast proliferation. Furthermore, LPA is known to function as a $Ca^{++}$-mobilizing agonist for a great variety of cell types. It has also been shown that exogenous LPA stimulates phospholipid hydrolysis via activation of phospholipase C or D, with subsequent $Ca^{++}$ mobilization and stimulation of protein kinase C, and that LPA can inhibit adenylate cyclase in a $G_i$-protein dependent manner.

Also, it has been found that LPA-induces shape changes in nerve cells and that LPA stimulates mitogen-activated protein (MAP) kinase by a G-protein-coupled process.

In A. Ridley, et al., The Small GTP-Binding Protein rho Regulates the Assembly of Focal Adhesions and Action Stress Fibers in Response to Growth Factors, Cell 70, 389–399 (1992), it was reported that LPA also is responsible for the ability of serum to cause actin stress fiber formation at focal adhesions inside cells.

LPA has also been shown to affect the binding of fibrinogen (as distinguished from fibronectin) to isolated platelet glycoprotein IIb–IIIa. S. Smyth, et al., Fibrinogen binding to purified platelet glycoprotein IIb–IIIa is modulated by lipids, J. Biol. Chem. 267: 155568–155577 (1992).

However, prior to our work, LPA had not been suggested to promote fibronectin binding on the external surfaces of cells.

SUMMARY OF THE INVENTION

We have discovered that LPA is a potent enhancer of fibronectin binding to mammalian (particularly human) cells, where the cell is of a type that in nature typically exhibits some fibronectin binding. Endothelial and epithelial tissue are preferred.

In one aspect, the invention provided a method for enhancing fibronectin binding the exterior of adherent cells. One exposes the cells to an exogenous supply of a lysophosphatidic acid (or a salt thereof), and also to fibronectin (exogenously or endogenously supplied). The supply is essentially free of protein from blood serum and protein from lipoprotein. The preferred cells are human cells, and the preferred lysophosphatidic acid is one that is also naturally occurring in humans.

In another aspect, the invention provides a kit for practicing the above method. A topical skin salve is provided that contains a lysophosphatidic acid (or salt thereof) and a liquid carrier. The kit also has instructions for applying the salve to the exterior of a mammal. The acid can be a lysophosphatidic acid of the type that is also naturally occurring in humans. The liquid can be a liquid in which the acid is soluble in (or suspendible in) such as water or albumin.

We believe that in mammals local tissue injury results in the leakage of blood protein and the activation of the clotting system. LPA is released from activated platelets. LPA then induces increases in the incorporation of fibronectin into the provisional matrix which serves as a substratum for cell migration. We speculate that antagonists of lysophosphatidic acids may prevent the over elaboration of binding (as in keloid or plaque formation or plaque).

The objects of the present invention therefore include:

(a) providing a method of the above kind to enhance fibronectin binding. This method would enhance wound healing, and may regulate tumor metastasis and atherogenesis. External application of an LPA salve to wounded skin should assist in the wound healing (at least in those cells that were previously able to bind fibronectin). With regard to metastasis, cancer cells lose their ability to bind fibronectin, thus enhancing migration to other areas of the body. Slowing the migration may slow the spread of the cancer. The invention may also assist in avoiding lesions after injury or when implants are given to humans by promoting more normal interior "wound" healing; and (b) providing a salve for the external applications for the above purposes. One such salve would be the sodium salt of 1-oleoyl lysophosphatidic acid in water, at a concentration of 100 ng/ml.

These and still other objects and advantages of the present invention will be apparent from the description below.

A BRIEF DESCRIPTION OF THE DRAWINGS

FIG. 1 is a schematic representation of 1-oleoyl lysophosphatidic acid. FIG. 2 is a schematic representation of a sodium salt of the compound of FIG. 1.

DESCRIPTION OF THE PREFERRED EMBODIMENTS

GENERAL OVERVIEW

Figure 1:
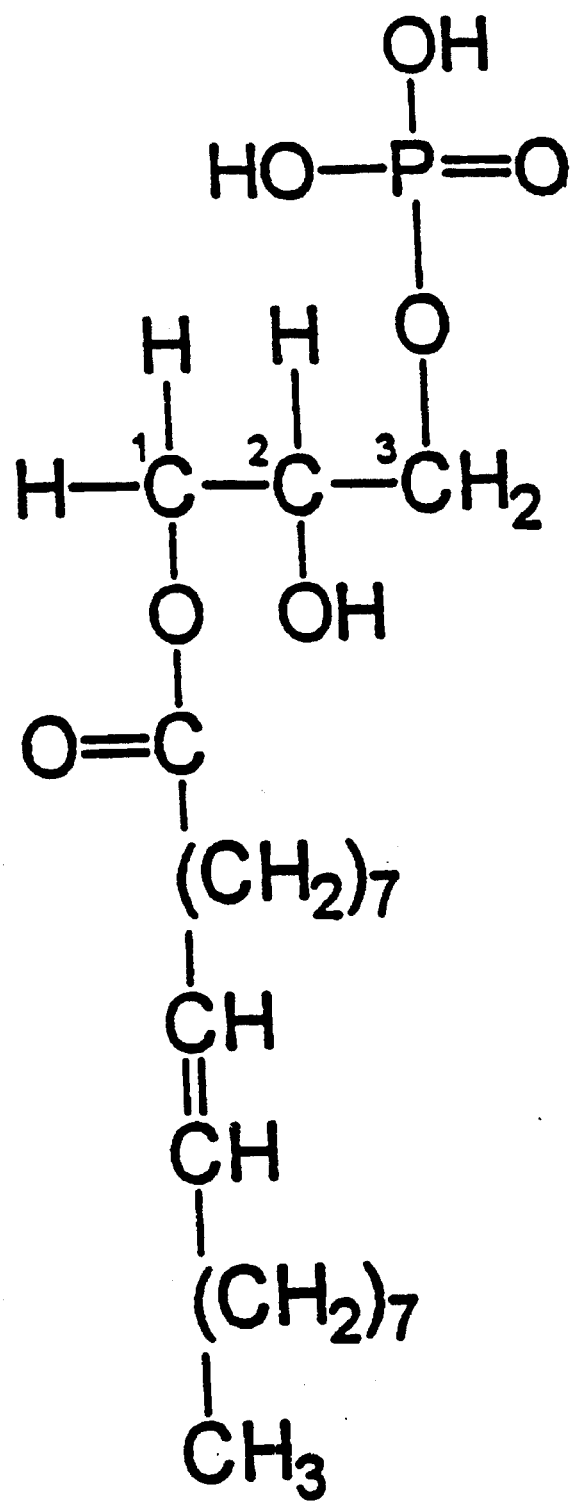
Figure 2:
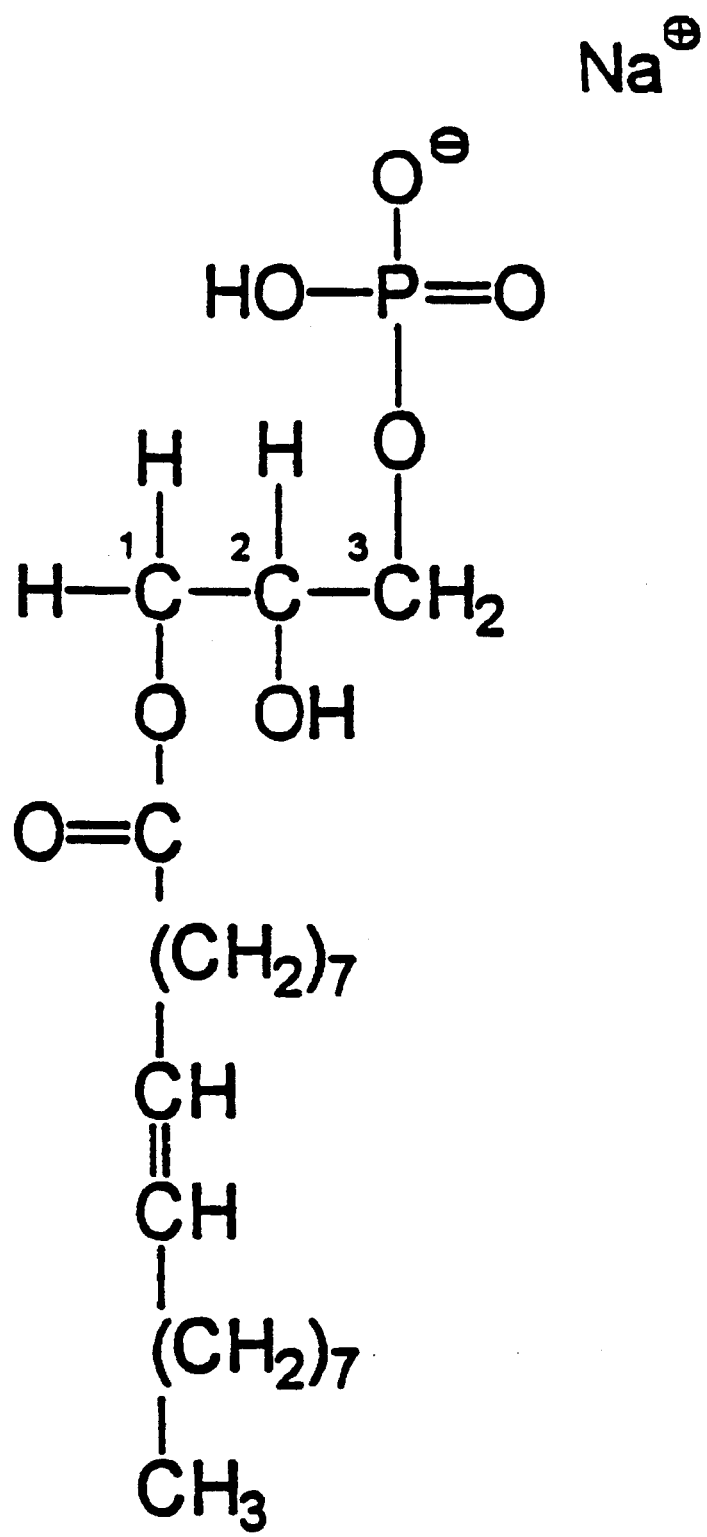

We have identified lysophosphatidic acids (and salts thereof) as potent enhancers of the binding and extra-cellular matrix deposition of fibronectin. The experiments below confirm the activities with cultured human fibroblasts, MG-63 osteosarcoma cells, and normal human foreskin fibroblasts. The 1-oleoyl, 1-palmitoyl, 1-stearoyl and 1-myristoyl forms of LPA increased $^{125}$I labelled fibronectin binding to cells. Other 1-position fatty acid esters (e.g. the ester of linoleic acid) should also work.

METHODS

The human osteosarcoma fibroblastic cell line MG-63 was obtained from the American Type Culture Collection (Rockville, Md.). Human foreskin fibroblasts (TJ) were a strain derived locally by Dr. Lynn Allen-Hoffmann, University of Wisconsin-Madison. Cells were cultured in Dulbecco's modified Eagle's medium (GIBCO, Gaithersburg, Md.) supplemented with 5% or 10% fetal bovine serum (Intergen, Purchase, N.Y.). All cells were seeded at 100,000 cells/2 cm2 well (24-well plates, Costar, Cambridge, Mass.) and were used 2–3 days after seeding.

Phospholipids were obtained from Sigma Chemical Co. (St. Louis, Mo.) or Avanti Polar Lipids (Birmingham, Ala.). Human plasma fibronectin was purified from fibronectin- and fibrinogen-rich by-product of factor VIII production. D. Mosher et al., In vitro formation of disulfide-bonded fibronectin . . . , J. Biol. Chem. 258: 6595–6601 (1983).

The 70 kDa amino-terminal, gelatin-binding fragment of fibronectin was generated and purified as previously described. P. McKeown-Longo, et al., Interaction of the 70,000-mol-wt-amino terminal fragment of fibronectin with the matrix-assembly receptor of fibroblasts, J. Cell Biol. 100: 363–374 (1985).

Iodinations of fibronectin (800 cpm/ng) and the 70 kDa fragment (1163 cpm/ng) were performed using the chloramine T method as previously described. A. Allio, et al., Extracellular matrix assembly of cell derived and plasma-derived fibronectins by substrate-attached fibroblasts, J. Cell. Physiol. 135:459–466 (1988).

Purity of labelled proteins was assessed by polyacrylamide gel electrophoresis in sodium dodecyl sulfate (SDS-PAGE) followed by autoradiography. Cell binding studies were done on confluent monolayers as described previously. W. Checovich, et al., Lipoproteins enhance fibronectin binding to adherent cells, Arteriosclerosis and Thrombosis, 12:1122–1130 (1992).

Cell layers were washed twice with Tris-buffered saline and preincubated in a standard medium (0.5 ml) containing 0.2% bovine serum albumin (fraction V, Sigma), 10 mM N-hydroxyethylpiperazine-N'-2-ethanesulfonic acid (HEPES, pH 7.4), and 10 ug/ml cycloheximide (Sigma). The cycloheximide was used routinely to avoid the possibly confounding effect of differences in synthesis of endogenous fibronectin and other proteins.

After 2 hours, the cells were washed once with Tris-buffered saline before the binding mixtures were added. The mixtures contained radiolabeled fibronectin (0.3 ug/ml, approximately 150,000 cpm/well) and unlabelled phospholipids at various concentrations in 0.5 ml of the same standard medium. After 45 minutes at 37 degrees C., the cell layers were washed three times with cold Tris-buffered saline and solubilized with 0.2 N NaOH, and the amount of total cell and matrix associated radioactivity was measured. Nonspecific binding in the presence of 500 ug/ml of unlabelled fibronectin (approximately 10–30% of total binding for intact fibronectin and the 70-kd fragment) was subtracted from total binding to calculate specific binding.

Fibronectin dose-response data were analyzed separately using the weighted non-linear least squares program LIGAND, as modified by G. A. McPherson (Elservier-BIOSOFT, Cambridge, UK). This analysis allowed for the deconvolution of the total binding curve to its specific and nonspecific components. Data were collated as nanograms bound per milligram of cell protein as determined by the method of Lowry et al., Protein measurement with the Folin phenol reagent. J. Biol. Chem. 193:265–275 (1951).

To test the activity of phospholipase A2, 20 ng of the acid were treated with 0.14 Units of enzyme, plus 2.5 mM calcium chloride, for 60 min. at 37° C. in TBS, then added directly to cycloheximide treated MG-63 cells for 45 minutes at a final concentration of 40 ng/ml. For phospholipase B, the acids were treated identically except that 0.12 Units of enzyme were used. Nonspecific binding in the presence of 500 ug/ml unlabelled fibronectin was also determined and subtracted from the total bound values. Nonspecific fibronectin binding did not vary between treatments. Calcium chloride was added to a final concentration of 2.5mM in all treatments.

RESULTS 1-oleoyl, lysophosphatidic acid enhanced fibronectin binding to human MG-63 osteosarcoma cells in a dose dependent manner. The average fold increase in fibronectin binding over several experiments was 2.2±std. dev., n=5). In MG-63 cells, LPA was minimally active at 0.2 nM and began to reach maximal activity at around 20 nM.

Normal human foreskin fibroblasts were also sensitive to this LPA, but the fold-increase was more variable, between 0.5 to 3. In these normal fibroblasts, LPA was maximally active above 200 nM.

Three other LPA that we tried also worked well (1-myristoyl; 1-palmitoyl; and 1-stearoyl).

By contrast, the serine, ethanolamine, choline, and inositol derivatives of LPA were not active with respect to fibrinogen binding. Also, 1,2 dioleoyl phosphatidic acid (PA) was active at approximately 4000 nM, albeit we believe due to contamination with LPA.

To confirm that the LPA is the active agent, LPA and PA were treated with phospholipases B and A2. Phospholipase B hydrolyzes both ester bonds linking fatty acids to the glycerol backbone of phospholipids and lysophospholipids. Phospholipase A2 only hydrolyzes the ester bond of the 2 position in phospholipids, converting them to lysophospholipids. Treatment of LPA or PA with phospholipase B resulted in no activity. By contrast, phospholipase A2 did not alter the activity of LPA, which already lacks an acyl group at the 2-position, but did increase the activity of PA.

LPA also enhanced the binding of the 70-kDa fragment fibronectin to MG-63 cells approximately three-fold (very comparable to the enhancement of whole fibronectin binding). Thus, this segment is likely the effected region.

We believe that LPA stimulates fibronectin matrix assembly due to LPA's interaction with G protein-coupled receptor and the subsequent stimulation of protein kinase C and inhibition of adenylate cyclase. Kinetic analysis indicated that the binding effect is likely due to an increased number of binding sites on cell external surfaces.

Although the present invention has been described with reference to certain preferred embodiments, other versions are possible. The scope of the claims should therefore not be limited to just the description of the preferred embodiments herein. The claims should be looked to judge the full scope of the invention.

For example, the fatty acid residues at the C-1 position need not be just those specifically tried herein. The naturally prevalent LPAs are preferred. However, the fatty acid ester used does not appear critical (as long as there is no fatty acid ester at the carbon 2 position).

A topically applied salve with the LPA content between 1 and 1000 ng/ml LPA could be dabbed against an open wound by itself, or we speculate possibly along with (or shortly before, or shortly after) a topically applied pain killer such as lidocaine.

For use in possibly reducing tumor migration (e.g. migration of a skin cancer), the LPAs could be injected into the tumor using a liquid carrier (e.g. water) with similar or higher molarities of LPA. We have not, to date, tried this.

In all cases, the key factor is providing an exogenous supply of the LPA (rather than relying just on the host's own resources). By "exogenous" we mean (in the case of a live host) LPA produced outside of that host.

We claim:

1. A method for enhancing fibronectin binding to endothelial or epithelial human cells in a skin wound, the method comprising the steps of:

exposing the cells to an exogenous supply of a lysophosphatidic acid in an amount sufficient to enhance said fibronectin binding, wherein the supply is essentially free of lipoprotein and protein from blood serum; and exposing those cells to fibronectin;

whereby fibronectin binding to the exterior of said cells is enhanced.

* * * * *

UNITED STATES PATENT AND TRADEMARK OFFICE
CERTIFICATE OF CORRECTION

PATENT NO.   : 5,480,877
DATED        : January 2, 1996
INVENTOR(S)  : Deane F. Mosher, Jr. and William J. Checovich It is certified that error appears in the above-identified patent and that said Letters Patent is hereby corrected as shown below:

Column 2, line 16        replace [iole] with i-ole

Column 2, line 22        insert "2" before the word carbon

Column 6, line 37,       add after the word "acid" or a salt thereof

Signed and Sealed this

Second Day of April, 1996

Attest:

BRUCE LEHMAN

Attesting Officer   Commissioner of Patents and Trademarks